(12) United States Patent
Nita et al.

(10) Patent No.: US 11,426,189 B2
(45) Date of Patent: *Aug. 30, 2022

(54) CONNECTOR FOR SECURING ULTRASOUND CATHETER TO TRANSDUCER

(71) Applicant: Flowcardia, Inc., Franklin Lakes, NJ (US)

(72) Inventors: Henry Nita, Redwood City, CA (US); Martinos Tran, Tracy, CA (US)

(*) Notice: Subject to any disclaimer, the term of this patent is extended or adjusted under 35 U.S.C. 154(b) by 627 days.

This patent is subject to a terminal disclaimer.

(21) Appl. No.: 16/430,580

(22) Filed: Jun. 4, 2019

(65) Prior Publication Data

US 2019/0282326 A1 Sep. 19, 2019

Related U.S. Application Data

(63) Continuation of application No. 15/256,233, filed on Sep. 2, 2016, now Pat. No. 10,349,964, which is a (Continued)

(51) Int. Cl.
*A61B 17/32* (2006.01)
*A61B 8/12* (2006.01)
(Continued)

(52) U.S. Cl.
CPC ........ *A61B 17/320068* (2013.01); *A61B 8/12* (2013.01); *A61B 8/445* (2013.01);
(Continued)

(58) Field of Classification Search
None
See application file for complete search history.

(56) References Cited

U.S. PATENT DOCUMENTS 3,296,620 A 1/1967 Rodda
3,433,226 A 3/1969 Boyd
(Continued)

FOREIGN PATENT DOCUMENTS

AU 2007240154 A1 1/2008
DE 2256127 A1 5/1974
(Continued)

OTHER PUBLICATIONS

Japanese Office Action for Japanese Application No. 2010-134566, dated Mar. 2, 2012.
(Continued)

*Primary Examiner* — Jonathan Cwern
(74) *Attorney, Agent, or Firm* — Dinsmore & Shohl LLP

(57) ABSTRACT

An ultrasonic system includes an ultrasound transducer housing, an ultrasonic catheter, and a transducer mechanism. The ultrasound transducer housing contains a transducer horn configured to be connected to a signal generator. The ultrasonic catheter includes an ultrasound transmission member having a proximal end and disposed in the lumen, a sonic connector that connects the proximal end of the ultrasound transmission member with the transducer horn, a control ring, and a nesting piece configured to selectively receive the sonic connector. The control ring is operatively coupled to the nesting piece to move the nesting piece. The transducer mechanism is configured to move from a first position to a second position, and wherein the transducer mechanism is configured such that movement of the transducer mechanism from the first position to the second position engages the control ring on the catheter to move the nesting piece.

14 Claims, 7 Drawing Sheets

Related U.S. Application Data continuation of application No. 14/169,009, filed on Jan. 30, 2014, now Pat. No. 9,433,433, which is a continuation of application No. 12/831,883, filed on Jul. 7, 2010, now Pat. No. 8,641,630, which is a continuation of application No. 11/192,749, filed on Jul. 29, 2005, now Pat. No. 7,758,510, which is a continuation of application No. 10/666,459, filed on Sep. 19, 2003, now Pat. No. 6,942,620.

(51) Int. Cl.
    *A61B 8/00*      (2006.01)
    *A61B 90/50*     (2016.01)
    *A61B 17/00*     (2006.01)

(52) U.S. Cl.
    CPC .... *A61B 90/50* (2016.02); *A61B 2017/00867* (2013.01); *A61B 2017/320069* (2017.08); *C08L 2201/12* (2013.01)

(56) References Cited

U.S. PATENT DOCUMENTS

| | | | |
|---|---|---|---|
| 3,443,226 A | 5/1969 | Knight |
| 3,565,062 A | 2/1971 | Kurls |
| 3,585,082 A | 6/1971 | Siller |
| 3,612,038 A | 10/1971 | Halligan |
| 3,631,848 A | 1/1972 | Muller |
| 3,679,378 A | 7/1972 | Van Impe et al. |
| 3,719,737 A | 3/1973 | Vaillancourt et al. |
| 3,739,460 A | 6/1973 | Addis et al. |
| 3,754,746 A | 8/1973 | Thiele |
| 3,823,717 A | 7/1974 | Pohlman et al. |
| 3,835,690 A | 9/1974 | Leonhardt et al. |
| 3,839,841 A | 10/1974 | Amplatz |
| 3,896,811 A | 7/1975 | Storz |
| 4,016,882 A | 4/1977 | Broadwin et al. |
| 4,033,331 A | 7/1977 | Guss et al. |
| 4,136,700 A | 1/1979 | Broadwin et al. |
| 4,337,090 A | 6/1982 | Harrison |
| 4,368,410 A | 1/1983 | Hance et al. |
| 4,417,578 A | 11/1983 | Banko |
| 4,425,115 A | 1/1984 | Wuchinich |
| 4,449,523 A | 5/1984 | Szachowicz et al. |
| 4,453,935 A | 6/1984 | Newton |
| 4,486,680 A | 12/1984 | Bonnet et al. |
| 4,505,767 A | 3/1985 | Quin |
| 4,535,759 A | 8/1985 | Polk et al. |
| 4,545,767 A | 10/1985 | Suzuki et al. |
| 4,565,589 A | 1/1986 | Harrison |
| 4,565,787 A | 1/1986 | Bossle et al. |
| 4,572,184 A | 2/1986 | Stohl et al. |
| 4,664,112 A | 5/1987 | Kensey et al. |
| 4,665,906 A | 5/1987 | Jervis |
| 4,679,558 A | 7/1987 | Kensey et al. |
| 4,700,705 A | 10/1987 | Kensey et al. |
| 4,721,117 A | 1/1988 | Mar et al. |
| 4,750,902 A | 6/1988 | Wuchinich et al. |
| 4,781,186 A | 11/1988 | Simpson et al. |
| 4,808,153 A | 2/1989 | Parisi |
| 4,811,743 A | 3/1989 | Stevens |
| 4,827,911 A | 5/1989 | Broadwin et al. |
| 4,838,853 A | 6/1989 | Parisi |
| 4,854,325 A | 8/1989 | Stevens |
| 4,870,953 A | 10/1989 | DonMicheal et al. |
| 4,886,060 A | 12/1989 | Wiksell |
| 4,920,954 A | 5/1990 | Alliger et al. |
| 4,923,462 A | 5/1990 | Stevens |
| 4,924,863 A | 5/1990 | Sterzer |
| 4,931,047 A | 6/1990 | Broadwin et al. |
| 4,936,281 A | 6/1990 | Stasz |
| 4,936,845 A | 6/1990 | Stevens |
| 4,979,952 A | 12/1990 | Kubota et al. |
| 5,000,185 A | 3/1991 | Yock |
| 5,015,227 A | 5/1991 | Broadwin et al. |
| 5,026,384 A | 6/1991 | Farr et al. |
| 5,030,201 A | 7/1991 | Palestrant |
| 5,030,357 A | 7/1991 | Lowe |
| 5,046,503 A | 9/1991 | Schneiderman |
| 5,053,008 A | 10/1991 | Bajaj |
| 5,058,570 A | 10/1991 | Idemoto et al. |
| 5,076,276 A | 12/1991 | Sakurai et al. |
| 5,091,205 A | 2/1992 | Fan |
| 5,100,423 A | 3/1992 | Fearnot |
| 5,109,859 A | 5/1992 | Jenkins |
| 5,114,414 A | 5/1992 | Buchbinder |
| 5,116,350 A | 5/1992 | Stevens |
| 5,127,917 A | 7/1992 | Niederhauser et al. |
| 5,131,393 A | 7/1992 | Ishiguro et al. |
| 5,156,143 A | 10/1992 | Bocquet et al. |
| 5,163,421 A | 11/1992 | Bernstein et al. |
| 5,171,216 A | 12/1992 | Dasse et al. |
| 5,180,363 A | 1/1993 | Idemoto et al. |
| 5,183,470 A | 2/1993 | Wettermann |
| 5,195,955 A | 3/1993 | Don Michael |
| 5,215,614 A | 6/1993 | Wijkamp et al. |
| 5,217,565 A | 6/1993 | Kou et al. |
| 5,221,255 A | 6/1993 | Mahurkar et al. |
| 5,226,421 A | 7/1993 | Frisbie et al. |
| 5,234,416 A | 8/1993 | Macaulay et al. |
| 5,236,414 A | 8/1993 | Takasu |
| 5,238,004 A | 8/1993 | Sahatjian et al. |
| 5,242,385 A | 9/1993 | Strukel |
| 5,243,997 A | 9/1993 | Uflacker et al. |
| 5,248,296 A | 9/1993 | Alliger |
| 5,255,669 A | 10/1993 | Kubota et al. |
| 5,267,954 A | 12/1993 | Nita |
| 5,269,291 A | 12/1993 | Carter |
| 5,269,297 A | 12/1993 | Weng et al. |
| 5,269,793 A | 12/1993 | Simpson |
| 5,279,546 A | 1/1994 | Mische et al. |
| 5,287,858 A | 2/1994 | Hammerslag et al. |
| 5,290,229 A | 3/1994 | Paskar |
| 5,304,115 A | 4/1994 | Pflueger et al. |
| 5,304,131 A | 4/1994 | Paskar |
| 5,312,328 A | 5/1994 | Nita et al. |
| 5,318,014 A | 6/1994 | Carter |
| 5,318,570 A | 6/1994 | Hood et al. |
| 5,324,255 A | 6/1994 | Passafaro et al. |
| 5,324,260 A | 6/1994 | O'Neill et al. |
| 5,325,860 A | 7/1994 | Seward et al. |
| 5,326,342 A | 7/1994 | Pflueger et al. |
| 5,328,004 A | 7/1994 | Fannin et al. |
| 5,329,927 A | 7/1994 | Gardineer et al. |
| 5,341,818 A | 8/1994 | Abrams et al. |
| 5,342,292 A | 8/1994 | Nita et al. |
| 5,344,395 A | 9/1994 | Whalen et al. |
| 5,346,502 A | 9/1994 | Estabrook et al. |
| 5,362,309 A | 11/1994 | Carter |
| 5,368,557 A | 11/1994 | Nita |
| 5,368,558 A | 11/1994 | Nita et al. |
| 5,376,084 A | 12/1994 | Bacich et al. |
| 5,378,234 A | 1/1995 | Hammerslag et al. |
| 5,380,274 A | 1/1995 | Nita |
| 5,380,316 A | 1/1995 | Aita et al. |
| 5,382,228 A | 1/1995 | Nita et al. |
| 5,383,460 A | 1/1995 | Jang et al. |
| 5,389,096 A | 2/1995 | Aita et al. |
| 5,391,144 A | 2/1995 | Sakurai et al. |
| 5,397,293 A | 3/1995 | Alliger et al. |
| 5,397,301 A | 3/1995 | Pflueger et al. |
| 5,403,324 A | 4/1995 | Ciervo et al. |
| 5,405,318 A | 4/1995 | Nita |
| 5,409,483 A | 4/1995 | Campbell et al. |
| 5,417,672 A | 5/1995 | Nita et al. |
| 5,417,703 A | 5/1995 | Brown et al. |
| 5,421,923 A | 6/1995 | Clarke et al. |
| 5,427,118 A | 6/1995 | Nita et al. |
| 5,431,168 A | 7/1995 | Webster, Jr. |
| 5,431,663 A | 7/1995 | Carter |
| 5,443,078 A | 8/1995 | Uflacker |
| 5,447,509 A | 9/1995 | Mills et al. |
| 5,449,369 A | 9/1995 | Imran |

(56) References Cited

U.S. PATENT DOCUMENTS

| | | |
|---|---|---|
| 5,449,370 A | 9/1995 | Vaitekunas |
| 5,451,209 A | 9/1995 | Ainsworth et al. |
| 5,462,529 A | 10/1995 | Simpson et al. |
| 5,465,733 A | 11/1995 | Hinohara et al. |
| 5,474,530 A | 12/1995 | Passafaro et al. |
| 5,474,531 A | 12/1995 | Carter |
| 5,480,379 A | 1/1996 | La Rosa |
| 5,484,398 A | 1/1996 | Stoddard |
| 5,487,757 A | 1/1996 | Truckai et al. |
| 5,498,236 A | 3/1996 | Dubrul et al. |
| 5,507,738 A | 4/1996 | Ciervo |
| 5,516,043 A | 5/1996 | Manna et al. |
| 5,527,273 A | 6/1996 | Manna et al. |
| 5,538,512 A | 7/1996 | Zenzon et al. |
| 5,540,656 A | 7/1996 | Pflueger et al. |
| 5,542,917 A | 8/1996 | Nita et al. |
| 5,597,497 A | 1/1997 | Dean et al. |
| 5,597,882 A | 1/1997 | Schiller et al. |
| 5,607,421 A | 3/1997 | Jeevanandam et al. |
| 5,611,807 A | 3/1997 | O'Boyle |
| 5,618,266 A | 4/1997 | Liprie |
| 5,626,593 A | 5/1997 | Imran |
| 5,627,365 A | 5/1997 | Chiba et al. |
| 5,649,935 A | 7/1997 | Kremer et al. |
| 5,658,282 A | 8/1997 | Daw et al. |
| 5,665,062 A | 9/1997 | Houser |
| 5,685,841 A | 11/1997 | Mackool |
| 5,695,460 A | 12/1997 | Siegel et al. |
| 5,695,507 A | 12/1997 | Auth et al. |
| 5,715,825 A | 2/1998 | Crowley |
| 5,720,724 A | 2/1998 | Ressemann et al. |
| 5,725,494 A | 3/1998 | Brisken |
| 5,728,062 A | 3/1998 | Brisken |
| 5,738,100 A | 4/1998 | Yagami et al. |
| 5,797,876 A | 8/1998 | Spears et al. |
| 5,816,923 A | 10/1998 | Milo et al. |
| 5,827,203 A | 10/1998 | Nita |
| 5,827,971 A | 10/1998 | Hale et al. |
| 5,830,127 A | 11/1998 | DeCastro |
| 5,830,222 A | 11/1998 | Makower |
| 5,846,218 A | 12/1998 | Brisken et al. |
| 5,873,835 A | 2/1999 | Hastings et al. |
| 5,876,385 A | 3/1999 | Ikari et al. |
| 5,893,838 A | 4/1999 | Daoud et al. |
| 5,895,397 A | 4/1999 | Jang et al. |
| 5,902,287 A | 5/1999 | Martin |
| 5,904,667 A | 5/1999 | Falwell |
| 5,916,192 A | 6/1999 | Nita et al. |
| 5,916,912 A | 6/1999 | Ames et al. |
| 5,935,142 A | 8/1999 | Hood |
| 5,935,144 A | 8/1999 | Estabrook |
| 5,937,301 A | 8/1999 | Gardner et al. |
| 5,944,737 A | 8/1999 | Tsonton et al. |
| 5,957,882 A | 9/1999 | Nita et al. |
| 5,957,899 A | 9/1999 | Spears et al. |
| 5,964,223 A | 10/1999 | Baran |
| 5,967,984 A | 10/1999 | Chu et al. |
| 5,971,949 A | 10/1999 | Levin et al. |
| 5,976,119 A | 11/1999 | Spears et al. |
| 5,989,208 A | 11/1999 | Nita |
| 5,989,275 A | 11/1999 | Estabrook et al. |
| 5,997,497 A | 12/1999 | Nita et al. |
| 6,004,280 A | 12/1999 | Buck et al. |
| 6,004,335 A | 12/1999 | Vaitekunas et al. |
| 6,007,499 A | 12/1999 | Martin et al. |
| 6,007,514 A | 12/1999 | Nita |
| 6,022,309 A | 2/2000 | Celliers et al. |
| 6,024,764 A | 2/2000 | Schroeppel |
| 6,029,671 A | 2/2000 | Stevens et al. |
| 6,030,357 A | 2/2000 | Daoud et al. |
| 6,036,689 A | 3/2000 | Tu et al. |
| 6,051,010 A | 4/2000 | DiMatteo et al. |
| 6,066,135 A | 5/2000 | Honda |
| 6,113,558 A | 9/2000 | Rosenschein et al. |
| 6,120,515 A | 9/2000 | Rogers et al. |
| 6,123,698 A | 9/2000 | Spears et al. |
| 6,142,971 A | 11/2000 | Daoud et al. |
| 6,149,596 A | 11/2000 | Bancroft |
| 6,159,176 A | 12/2000 | Broadwin et al. |
| 6,159,187 A | 12/2000 | Park et al. |
| 6,165,127 A | 12/2000 | Crowley |
| 6,165,188 A | 12/2000 | Saadat et al. |
| 6,179,809 B1 | 1/2001 | Khairkhahan et al. |
| 6,180,059 B1 | 1/2001 | Divino, Jr. et al. |
| 6,190,353 B1 | 2/2001 | Makower et al. |
| 6,206,842 B1 | 3/2001 | Tu et al. |
| 6,210,356 B1 | 4/2001 | Anderson et al. |
| 6,217,543 B1 | 4/2001 | Anis et al. |
| 6,217,565 B1 | 4/2001 | Cohen |
| 6,217,588 B1 | 4/2001 | Jerger et al. |
| 6,221,015 B1 | 4/2001 | Yock |
| 6,231,546 B1 | 5/2001 | Milo et al. |
| 6,231,587 B1 | 5/2001 | Makower |
| 6,235,007 B1 | 5/2001 | Divino, Jr. et al. |
| 6,241,692 B1 | 6/2001 | Tu et al. |
| 6,241,703 B1 | 6/2001 | Levin et al. |
| 6,241,744 B1 | 6/2001 | Imran et al. |
| 6,248,087 B1 | 6/2001 | Spears et al. |
| 6,277,084 B1 | 8/2001 | Abele et al. |
| 6,283,983 B1 | 9/2001 | Makower et al. |
| 6,287,271 B1 | 9/2001 | Dubrul et al. |
| 6,287,285 B1 | 9/2001 | Michal et al. |
| 6,287,317 B1 | 9/2001 | Makower et al. |
| 6,296,620 B1 | 10/2001 | Gesswein et al. |
| 6,298,620 B1 | 10/2001 | Hatzinikolas |
| 6,302,875 B1 | 10/2001 | Makower et al. |
| 6,309,358 B1 | 10/2001 | Okubo |
| 6,315,741 B1 | 11/2001 | Martin et al. |
| 6,315,754 B1 | 11/2001 | Daoud et al. |
| 6,331,171 B1 | 12/2001 | Cohen |
| 6,346,192 B2 | 2/2002 | Buhr et al. |
| 6,379,378 B1 | 4/2002 | Werneth et al. |
| 6,387,109 B1 | 5/2002 | Davison et al. |
| 6,387,324 B1 | 5/2002 | Patterson et al. |
| 6,394,956 B1 | 5/2002 | Chandrasekaran et al. |
| 6,398,736 B1 | 6/2002 | Seward |
| 6,409,673 B2 | 6/2002 | Yock |
| 6,416,533 B1 | 7/2002 | Gobin et al. |
| 6,423,026 B1 | 7/2002 | Gesswein et al. |
| 6,427,118 B1 | 7/2002 | Suzuki |
| 6,433,464 B2 | 8/2002 | Jones |
| 6,434,418 B1 | 8/2002 | Neal et al. |
| 6,450,975 B1 | 9/2002 | Brennan et al. |
| 6,454,737 B1 | 9/2002 | Nita et al. |
| 6,454,757 B1 | 9/2002 | Nita et al. |
| 6,454,997 B1 | 9/2002 | Divino, Jr. et al. |
| 6,484,052 B1 | 11/2002 | Visuri et al. |
| 6,491,707 B2 | 12/2002 | Makower et al. |
| 6,494,891 B1 | 12/2002 | Cornish et al. |
| 6,494,894 B2 | 12/2002 | Mirarchi |
| 6,500,141 B1 | 12/2002 | Irion et al. |
| 6,508,781 B1 | 1/2003 | Brennan et al. |
| 6,508,784 B1 | 1/2003 | Shu |
| 6,511,458 B2 | 1/2003 | Milo et al. |
| 6,514,249 B1 | 2/2003 | Maguire et al. |
| 6,524,251 B2 | 2/2003 | Rabiner et al. |
| 6,533,766 B1 | 3/2003 | Patterson et al. |
| 6,544,215 B1 | 4/2003 | Bencini et al. |
| 6,547,754 B1 | 4/2003 | Evans et al. |
| 6,547,788 B1 | 4/2003 | Maguire et al. |
| 6,551,337 B1 | 4/2003 | Rabiner et al. |
| 6,554,846 B2 | 4/2003 | Hamilton et al. |
| 6,555,059 B1 | 4/2003 | Myrick et al. |
| 6,558,502 B2 | 5/2003 | Divino, Jr. et al. |
| 6,562,031 B2 | 5/2003 | Chandrasekaran et al. |
| 6,573,470 B1 | 6/2003 | Brown et al. |
| 6,576,807 B1 | 6/2003 | Brunelot et al. |
| 6,582,387 B2 | 6/2003 | Derek et al. |
| 6,589,253 B1 | 7/2003 | Cornish et al. |
| 6,595,989 B1 | 7/2003 | Schaer |
| 6,596,235 B2 | 7/2003 | Divino, Jr. et al. |
| 6,602,467 B1 | 8/2003 | Divino, Jr. et al. |
| 6,602,468 B2 | 8/2003 | Patterson et al. |
| 6,605,217 B2 | 8/2003 | Buhr et al. |

(56) References Cited

U.S. PATENT DOCUMENTS

| | | |
|---|---|---|
| 6,607,698 B1 | 8/2003 | Spears et al. |
| 6,610,077 B1 | 8/2003 | Hancock et al. |
| 6,613,280 B2 | 9/2003 | Myrick et al. |
| 6,615,062 B2 | 9/2003 | Ryan et al. |
| 6,616,617 B1 | 9/2003 | Ferrera et al. |
| 6,622,542 B2 | 9/2003 | Derek et al. |
| 6,623,448 B2 | 9/2003 | Slater |
| 6,635,017 B1 | 10/2003 | Moehring et al. |
| 6,650,923 B1 | 11/2003 | Lesh et al. |
| 6,652,547 B2 | 11/2003 | Rabiner et al. |
| 6,660,013 B2 | 12/2003 | Rabiner et al. |
| 6,676,900 B1 | 1/2004 | Divino, Jr. et al. |
| 6,682,502 B2 | 1/2004 | Bond et al. |
| 6,685,657 B2 | 2/2004 | Jones |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,810 B2 | 2/2004 | Peacock, III et al. |
| 6,702,748 B1 | 3/2004 | Nita et al. |
| 6,702,750 B2 | 3/2004 | Yock |
| 6,719,715 B2 | 4/2004 | Newman et al. |
| 6,719,725 B2 | 4/2004 | Milo et al. |
| 6,729,334 B1 | 5/2004 | Baran |
| 6,733,451 B2 | 5/2004 | Rabiner et al. |
| 6,758,846 B2 | 7/2004 | Goble et al. |
| 6,761,698 B2 | 7/2004 | Shibata et al. |
| 6,814,727 B2 | 11/2004 | Mansouri-Ruiz |
| 6,855,123 B2 | 2/2005 | Nita |
| 6,866,670 B2 | 3/2005 | Rabiner et al. |
| 6,936,025 B1 | 8/2005 | Evans et al. |
| 6,936,056 B2 | 8/2005 | Nash et al. |
| 6,942,620 B2 * | 9/2005 | Nita ................ A61B 17/22004 600/459 |
| 6,942,677 B2 | 9/2005 | Nita et al. |
| 6,955,680 B2 | 10/2005 | Satou et al. |
| 7,004,173 B2 | 2/2006 | Sparks et al. |
| 7,004,176 B2 | 2/2006 | Lau |
| 7,056,294 B2 | 6/2006 | Khairkhahan et al. |
| 7,131,983 B2 | 11/2006 | Murakami |
| 7,137,963 B2 | 11/2006 | Nita et al. |
| 7,149,587 B2 | 12/2006 | Wardle et al. |
| 7,150,853 B2 | 12/2006 | Lee et al. |
| 7,166,098 B1 | 1/2007 | Steward et al. |
| 7,220,233 B2 | 5/2007 | Nita et al. |
| 7,267,650 B2 | 9/2007 | Chow et al. |
| 7,297,131 B2 | 11/2007 | Nita |
| 7,335,180 B2 | 2/2008 | Nita et al. |
| 7,341,569 B2 | 3/2008 | Soltani et al. |
| 7,384,407 B2 | 6/2008 | Rodriguez et al. |
| 7,393,338 B2 | 7/2008 | Nita |
| 7,421,900 B2 | 9/2008 | Karasawa et al. |
| 7,425,198 B2 | 9/2008 | Moehring et al. |
| 7,494,468 B2 | 2/2009 | Rabiner et al. |
| 7,503,895 B2 | 3/2009 | Rabiner et al. |
| 7,540,852 B2 | 6/2009 | Nita et al. |
| 7,604,608 B2 | 10/2009 | Nita et al. |
| 7,621,902 B2 | 11/2009 | Nita et al. |
| 7,621,929 B2 | 11/2009 | Nita et al. |
| 7,628,763 B2 | 12/2009 | Noriega et al. |
| 7,648,478 B2 | 1/2010 | Soltani et al. |
| 7,758,510 B2 * | 7/2010 | Nita ................ A61B 17/320068 600/459 |
| 7,771,358 B2 | 8/2010 | Moehring et al. |
| 7,771,452 B2 | 8/2010 | Pal et al. |
| 7,775,994 B2 | 8/2010 | Lockhart |
| 7,776,025 B2 | 8/2010 | Bobo, Jr. |
| 7,819,013 B2 | 10/2010 | Chan et al. |
| 7,850,623 B2 | 12/2010 | Griffin et al. |
| 7,918,819 B2 | 4/2011 | Karmarkar et al. |
| 7,935,108 B2 | 5/2011 | Baxter et al. |
| 7,938,819 B2 | 5/2011 | Kugler et al. |
| 7,942,809 B2 | 5/2011 | Leban |
| 7,955,293 B2 | 6/2011 | Nita et al. |
| 7,993,308 B2 | 8/2011 | Rule et al. |
| 8,038,693 B2 | 10/2011 | Allen |
| 8,043,251 B2 | 10/2011 | Nita et al. |
| 8,052,607 B2 | 11/2011 | Byrd |
| 8,083,727 B2 | 12/2011 | Kugler et al. |
| 8,133,236 B2 | 3/2012 | Nita |
| 8,152,753 B2 | 4/2012 | Nita et al. |
| 8,172,758 B2 | 5/2012 | Harhen |
| 8,221,343 B2 | 7/2012 | Nita et al. |
| 8,226,566 B2 | 7/2012 | Nita |
| 8,246,643 B2 | 8/2012 | Nita |
| 8,257,378 B1 | 9/2012 | O'Connor |
| 8,308,677 B2 | 11/2012 | Nita et al. |
| 8,343,134 B2 | 1/2013 | Kost et al. |
| 8,414,543 B2 | 4/2013 | Mcguckin, Jr. et al. |
| 8,496,669 B2 | 7/2013 | Nita et al. |
| 8,506,519 B2 | 8/2013 | Nita |
| 8,613,700 B2 | 12/2013 | Ueno et al. |
| 8,613,751 B2 | 12/2013 | Nita et al. |
| 8,617,096 B2 | 12/2013 | Nita et al. |
| 8,632,560 B2 | 1/2014 | Pal et al. |
| 8,641,630 B2 * | 2/2014 | Nita ................ A61B 90/50 600/466 |
| 8,647,293 B2 | 2/2014 | Nita |
| 8,647,296 B2 | 2/2014 | Moberg et al. |
| 8,663,259 B2 | 3/2014 | Levine et al. |
| 8,668,709 B2 | 3/2014 | Nita et al. |
| 8,690,818 B2 | 4/2014 | Bennett et al. |
| 8,690,819 B2 | 4/2014 | Nita et al. |
| 8,702,595 B2 | 4/2014 | Ueki |
| 8,708,892 B2 | 4/2014 | Sugiyama et al. |
| 8,708,994 B2 | 4/2014 | Pettis et al. |
| 8,725,228 B2 | 5/2014 | Koblish et al. |
| 8,764,700 B2 | 7/2014 | Zhang et al. |
| 8,768,433 B2 | 7/2014 | Jenkins et al. |
| 8,790,291 B2 | 7/2014 | Nita et al. |
| 8,974,446 B2 | 3/2015 | Nguyen et al. |
| 8,978,478 B2 | 3/2015 | Ishioka |
| 9,101,387 B2 | 8/2015 | Plowe et al. |
| 9,107,590 B2 | 8/2015 | Hansmann et al. |
| 9,237,837 B2 | 1/2016 | Omoto et al. |
| 9,265,520 B2 | 2/2016 | Nita |
| 9,282,984 B2 | 3/2016 | Nita |
| 9,314,258 B2 | 4/2016 | Nita et al. |
| 9,381,027 B2 | 7/2016 | Nita et al. |
| 9,421,024 B2 | 8/2016 | Nita et al. |
| 9,433,433 B2 * | 9/2016 | Nita ................ A61B 17/320068 |
| 9,603,615 B2 | 3/2017 | Sarge |
| 9,770,250 B2 | 9/2017 | Nita et al. |
| 9,955,994 B2 | 5/2018 | Nita |
| 10,004,520 B2 | 6/2018 | Nita et al. |
| 10,130,380 B2 | 11/2018 | Nita et al. |
| 10,349,964 B2 * | 7/2019 | Nita ................ A61B 8/445 |
| 2002/0022858 A1 | 2/2002 | Demond et al. |
| 2002/0049409 A1 | 4/2002 | Noda et al. |
| 2002/0077550 A1 | 6/2002 | Rabiner et al. |
| 2002/0188276 A1 | 12/2002 | Evans et al. |
| 2002/0189357 A1 | 12/2002 | Lai et al. |
| 2003/0009153 A1 | 1/2003 | Brisken et al. |
| 2003/0036705 A1 | 2/2003 | Hare et al. |
| 2003/0040762 A1 | 2/2003 | Dorros et al. |
| 2003/0199817 A1 | 10/2003 | Thompson et al. |
| 2003/0216732 A1 | 11/2003 | Truckai et al. |
| 2003/0225332 A1 | 12/2003 | Okada et al. |
| 2004/0019349 A1 | 1/2004 | Fuimaono et al. |
| 2004/0024393 A1 | 2/2004 | Nita et al. |
| 2004/0054367 A1 | 3/2004 | Teodoro, Jr. et al. |
| 2004/0164030 A1 | 8/2004 | Lowe et al. |
| 2004/0167511 A1 | 8/2004 | Buehlmann et al. |
| 2004/0193033 A1 | 9/2004 | Badehi et al. |
| 2005/0033311 A1 | 2/2005 | Guldfeldt et al. |
| 2005/0149110 A1 | 7/2005 | Wholey et al. |
| 2005/0165388 A1 | 7/2005 | Bhola |
| 2005/0171527 A1 | 8/2005 | Bhola |
| 2005/0228286 A1 | 10/2005 | Messerly et al. |
| 2006/0074441 A1 | 4/2006 | Mcguckin, Jr. et al. |
| 2006/0149169 A1 | 7/2006 | Nunomura et al. |
| 2006/0206039 A1 | 9/2006 | Wilson et al. |
| 2006/0264809 A1 | 11/2006 | Hansmann et al. |
| 2007/0032749 A1 | 2/2007 | Overall et al. |
| 2007/0161945 A1 | 7/2007 | Nita et al. |

(56) References Cited

U.S. PATENT DOCUMENTS

| | | |
|---|---|---|
| 2007/0178768 A1 | 8/2007 | Harshman et al. |
| 2008/0033284 A1 | 2/2008 | Hauck |
| 2008/0071343 A1 | 3/2008 | Mayberry et al. |
| 2008/0208084 A1 | 8/2008 | Horzewski et al. |
| 2008/0221506 A1 | 9/2008 | Rodriguez et al. |
| 2008/0294037 A1 | 11/2008 | Richter |
| 2009/0017293 A1 | 1/2009 | Arai et al. |
| 2009/0143795 A1 | 6/2009 | Robertson |
| 2010/0004558 A1 | 1/2010 | Frankhouser et al. |
| 2010/0023037 A1 | 1/2010 | Nita et al. |
| 2010/0069854 A1 | 3/2010 | Okoh et al. |
| 2010/0076454 A1 | 3/2010 | Bos |
| 2010/0121144 A1 | 5/2010 | Farhadi |
| 2010/0217306 A1 | 8/2010 | Raabe et al. |
| 2010/0268206 A1 | 10/2010 | Manwaring et al. |
| 2011/0046522 A1 | 2/2011 | Chan et al. |
| 2011/0105960 A1 | 5/2011 | Wallace |
| 2011/0130834 A1 | 6/2011 | Wilson et al. |
| 2011/0196399 A1 | 8/2011 | Robertson et al. |
| 2011/0196403 A1 | 8/2011 | Robertson et al. |
| 2011/0237982 A1 | 9/2011 | Wallace |
| 2011/0313328 A1 | 12/2011 | Nita |
| 2012/0010506 A1 | 1/2012 | Ullrich |
| 2012/0109021 A1 | 5/2012 | Hastings et al. |
| 2012/0130475 A1 | 5/2012 | Shaw |
| 2012/0217306 A1 | 8/2012 | Morrill Webb et al. |
| 2012/0238916 A1 | 9/2012 | Nita et al. |
| 2012/0238946 A1 | 9/2012 | Nita et al. |
| 2012/0311844 A1 | 12/2012 | Nita et al. |
| 2012/0330196 A1 | 12/2012 | Nita |
| 2013/0046297 A1 | 2/2013 | Lingeman et al. |
| 2013/0060169 A1 | 3/2013 | Yamada |
| 2013/0331652 A1 | 12/2013 | Okamoto |
| 2013/0338580 A1 | 12/2013 | Yamatani et al. |
| 2014/0005706 A1 | 1/2014 | Gelfand et al. |
| 2014/0012087 A1 | 1/2014 | Omoto |
| 2014/0039491 A1 | 2/2014 | Bakos et al. |
| 2014/0171804 A1 | 6/2014 | Van Hoven |
| 2014/0236118 A1 | 8/2014 | Unser et al. |
| 2014/0243712 A1 | 8/2014 | Humayun et al. |
| 2014/0350401 A1 | 11/2014 | Sinelnikov |
| 2014/0358028 A1 | 12/2014 | Vetter et al. |
| 2014/0358029 A1 | 12/2014 | Vetter et al. |
| 2015/0025544 A1 | 1/2015 | Nita et al. |
| 2015/0073357 A1 | 3/2015 | Bagwell et al. |
| 2015/0105621 A1 | 4/2015 | Farhadi |
| 2015/0105715 A1 | 4/2015 | Pikus et al. |
| 2015/0133918 A1 | 5/2015 | Sachar |
| 2015/0148795 A1 | 5/2015 | Amos et al. |
| 2015/0157443 A1 | 6/2015 | Hauser et al. |
| 2015/0190660 A1 | 7/2015 | Sarge et al. |
| 2015/0297258 A1 | 10/2015 | Escudero et al. |
| 2015/0359651 A1 | 12/2015 | Wübbeling |
| 2016/0128717 A1 | 5/2016 | Nita |
| 2016/0128767 A1 | 5/2016 | Azamian et al. |
| 2016/0135835 A1 | 5/2016 | Onuma |
| 2016/0183956 A1 | 6/2016 | Nita |
| 2016/0271362 A1 | 9/2016 | Van Liere |
| 2016/0328998 A1 | 11/2016 | Nita et al. |
| 2016/0338722 A1 | 11/2016 | Nita et al. |
| 2016/0367284 A1 | 12/2016 | Nita et al. |
| 2017/0065288 A1 | 3/2017 | Imai et al. |
| 2017/0128090 A1 | 5/2017 | Sarge |
| 2017/0224375 A1 | 8/2017 | Robertson et al. |
| 2017/0265879 A1 | 9/2017 | Washburn, II et al. |
| 2017/0265886 A1 | 9/2017 | Nita et al. |
| 2017/0354428 A1 | 12/2017 | Nita et al. |
| 2018/0042636 A1 | 2/2018 | Nita |
| 2018/0140321 A1 | 5/2018 | Deepa |
| 2018/0168668 A1 | 6/2018 | Zheng |
| 2018/0177515 A1 | 6/2018 | Boyle et al. |
| 2018/0197856 A1 | 7/2018 | Chou et al. |
| 2018/0221040 A1 | 8/2018 | Roll Hoye |
| 2018/0280005 A1 | 10/2018 | Parmentier |
| 2018/0280044 A1 | 10/2018 | Nita et al. |

FOREIGN PATENT DOCUMENTS

| | | |
|---|---|---|
| DE | 2438648 A1 | 2/1976 |
| DE | 8910040 U1 | 12/1989 |
| DE | 3821836 A1 | 1/1990 |
| DE | 4042435 C2 | 2/1994 |
| DE | 10146011 A1 | 4/2003 |
| EP | 0005719 A1 | 12/1979 |
| EP | 0316789 A2 | 5/1989 |
| EP | 0316796 A2 | 5/1989 |
| EP | 0376562 A2 | 7/1990 |
| EP | 0379156 A2 | 7/1990 |
| EP | 0394583 A2 | 10/1990 |
| EP | 0443256 A1 | 8/1991 |
| EP | 0472368 A2 | 2/1992 |
| EP | 0541249 A2 | 5/1993 |
| EP | 0820728 A2 | 1/1998 |
| EP | 1323481 A2 | 7/2003 |
| GB | 1106957 | 3/1968 |
| JP | H2-7150 U | 10/1988 |
| JP | 01-099547 | 4/1989 |
| JP | 6086822 A | 3/1994 |
| JP | H07500752 A | 1/1995 |
| JP | 7116260 A | 5/1995 |
| JP | 9-503137 | 3/1997 |
| JP | 10-216140 | 8/1998 |
| JP | 2000-291543 | 10/2000 |
| JP | 2001-104356 | 4/2001 |
| JP | 2001-321388 | 11/2001 |
| JP | 2002-186627 | 7/2002 |
| JP | 2005-253874 | 9/2005 |
| JP | 2006-522644 A | 10/2006 |
| JP | 2007512087 A | 5/2007 |
| JP | 2007520255 A | 7/2007 |
| WO | 8705739 A1 | 9/1987 |
| WO | 8705793 A1 | 10/1987 |
| WO | 8906515 A1 | 7/1989 |
| WO | 9001300 A1 | 2/1990 |
| WO | 9004362 A1 | 5/1990 |
| WO | 9107917 A2 | 6/1991 |
| WO | 9211815 A2 | 7/1992 |
| WO | 9308750 A2 | 5/1993 |
| WO | 9316646 A1 | 9/1993 |
| WO | 9412140 A1 | 6/1994 |
| WO | 9414382 A1 | 7/1994 |
| WO | 9508954 A1 | 4/1995 |
| WO | 9509571 A1 | 4/1995 |
| WO | 9515192 A1 | 6/1995 |
| WO | 9635469 A1 | 11/1996 |
| WO | 9705739 A1 | 2/1997 |
| WO | 9721462 A1 | 6/1997 |
| WO | 9745078 A1 | 12/1997 |
| WO | 9827874 A1 | 7/1998 |
| WO | 9835721 A2 | 8/1998 |
| WO | 9851224 A2 | 11/1998 |
| WO | 9852637 A1 | 11/1998 |
| WO | 9925412 A2 | 5/1999 |
| WO | 0053341 A1 | 9/2000 |
| WO | 0067830 A1 | 11/2000 |
| WO | 02094103 A1 | 11/2002 |
| WO | 03039381 A1 | 5/2003 |
| WO | 2004012609 A1 | 2/2004 |
| WO | 2004093736 A2 | 11/2004 |
| WO | 2004112888 A2 | 12/2004 |
| WO | 2005053769 A2 | 6/2005 |
| WO | 2005112770 A1 | 12/2005 |
| WO | 2006049593 A1 | 5/2006 |
| WO | 2013109269 A1 | 7/2013 |
| WO | 2014022716 A2 | 2/2014 |
| WO | 2014105754 A1 | 7/2014 |
| WO | 2014106847 A1 | 7/2014 |
| WO | 2018097856 A1 | 5/2018 |
| WO | 20180187159 A1 | 10/2018 |

OTHER PUBLICATIONS

Sehgal, et al., Ultrasound-Assisted Thrombolysis, Investigative Radiology, 1993, vol. 28, Issue 10, pp. 939-943.

(56) References Cited

OTHER PUBLICATIONS

Siegel, et al., "In Vivo Ultrasound Arterial Recanalization of Atherosclerotic Total Occlusions", Journal of the American College of Cardiology, Feb. 1990, vol. 15, No. 2, pp. 345-351.
"What is Electron Beam Curing?" downloaded from web on Nov. 14, 2002,4 pages total. <http://www.ms.oml.gov/researchgroups/composites/new%20orccmt%20pages/pages/ebwha>.
EP Extended Search Report dated Aug. 13, 2009; Application 04710537.5-1269, 5 pages.
Noone, D.: Experimental and Numerical Investigation of Wire Waveguides for Therapeutic Ultrasound Angioplasty. M.Eng. Dublin City University. 2008.
Definition of the term "connected", retrieved on Sep. 21, 2013. <www.thefreedictionary.com/connected> 1 page total.
Supplemental European Search Report dated Nov. 5, 2009 for European Application No. EP03766931.
International Search Report dated Oct. 28, 2003 for PCT Application No. PCT/US2003/023468.
Extended European Search Report dated Mar. 22, 2012 for European Application No. EP11188799.
International Search Report dated Dec. 23, 2005 for PCT Application No. PCT/US2004/019378.
Extended European Search Report for Patent Application No. 06718204.8, dated May 30, 2012.
International Search Report dated Aug. 1, 2013 for PCT Application No. PCT/US2013/053306.
International Preliminary Report dated Aug. 1, 2013 for PCT Application No. PCT/US2013/053306.
Written Opinion dated Aug. 1, 2013 for PCT Application No. PCT/US2013/053306.
Supplemental European Search Report dated Apr. 29, 2009 for European Application No. EP 04711207.3.
Office Action dated Aug. 3, 2010 from Japanese Application No. 2006-517355 filed on Jun. 16, 2004.
Office Action dated Jan. 26, 2010 from Japanese Application No. 2006-517355 filed on Jun. 16, 2004.
International Preliminary Report and Written Opinion dated Aug. 1, 2017 for PCT Application No. PCT/US2017/030675.
International Preliminary Report and Written Opinion dated Feb. 6, 2018 for PCT Application No. PCT/US2018/017022.
Extended European Search Report dated Mar. 5, 2012 for European Application No. 12153606.4-1269.
Margaret Fyfe et al., Mast cell degranulation and increased vascular permeability induced by therapeutic' ultrasound in the rate ankle joint, Br. J. exp. Path., 1984, vol. 65, pp. 671-676.
"Irradiation, Biological, and Other Technologies: E-beam, Biological, and Sharps Treatment Systems", Non-Incineration Medical Waste Treatment Technologies, Aug. 2001, Chapter 9, pp. 69-74, Health Care Without Harm, Washington, DC.
Paul Yock et al., Catheter-Based Ultrasound Thrombolysis Shake, Rattle, and Repertuse, https://doi.org/10.1161/01.CIR.95.6.1360 Circulation. 1997;95:1360-1362 Originally published Mar. 18, 1997.
Calhoun et al., "Electron-Beam Systems for Medical Device Sterilization", downloaded from web on Oct. 8, 2002 <http://www.devicelink.com/mpb/archive/97/07/002.html> 7 pages total.
Definition of the term "coupled", retrieved on May 18, 2013. <http://www.merriam-webster.com/dictionary/couple> 1 page total.
"E-Beam Theory" RDI-IBA Technology Group, downloaded from web on Oct. 8, 2002 <http://www.e-beamrdi/EbeamTheory.htm> 2 pages total.
Office Action dated May 20, 2010 from Japanese Application No. 2006-541200 filed on Oct. 25, 2004.
Office Action dated Oct. 11, 2012 from Japanese Application No. 2010-181956.

\* cited by examiner

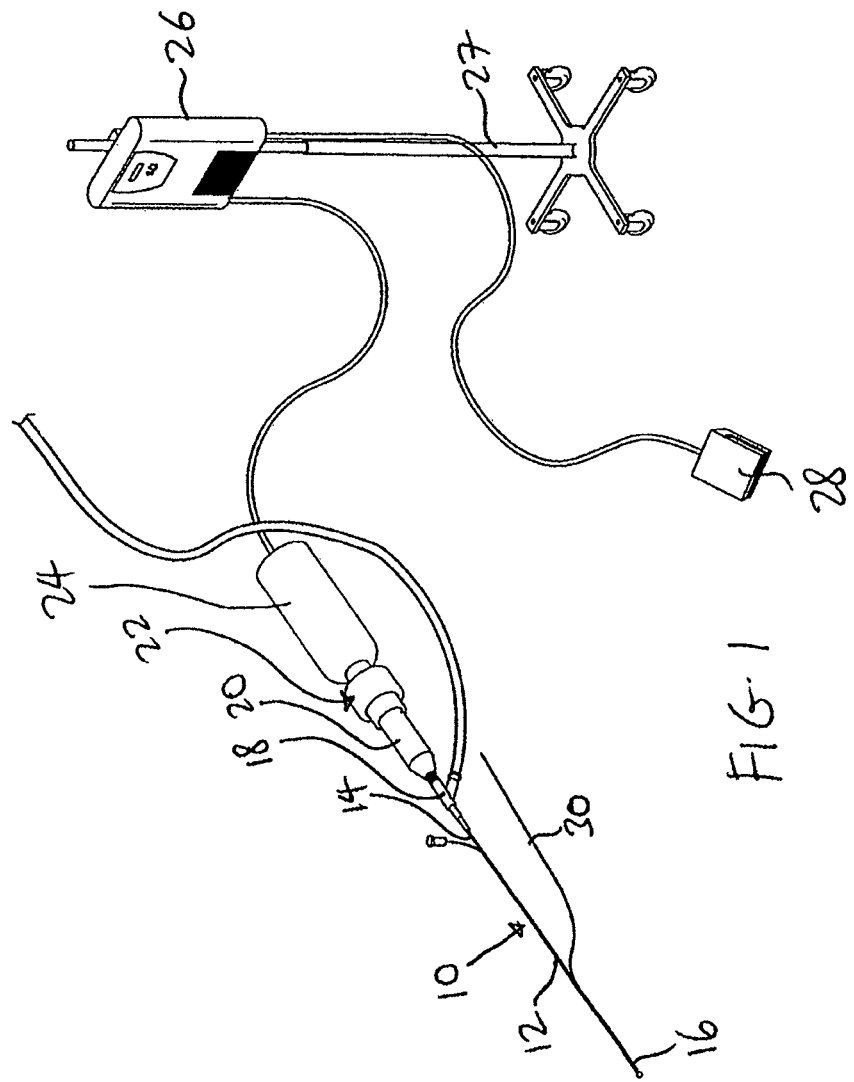

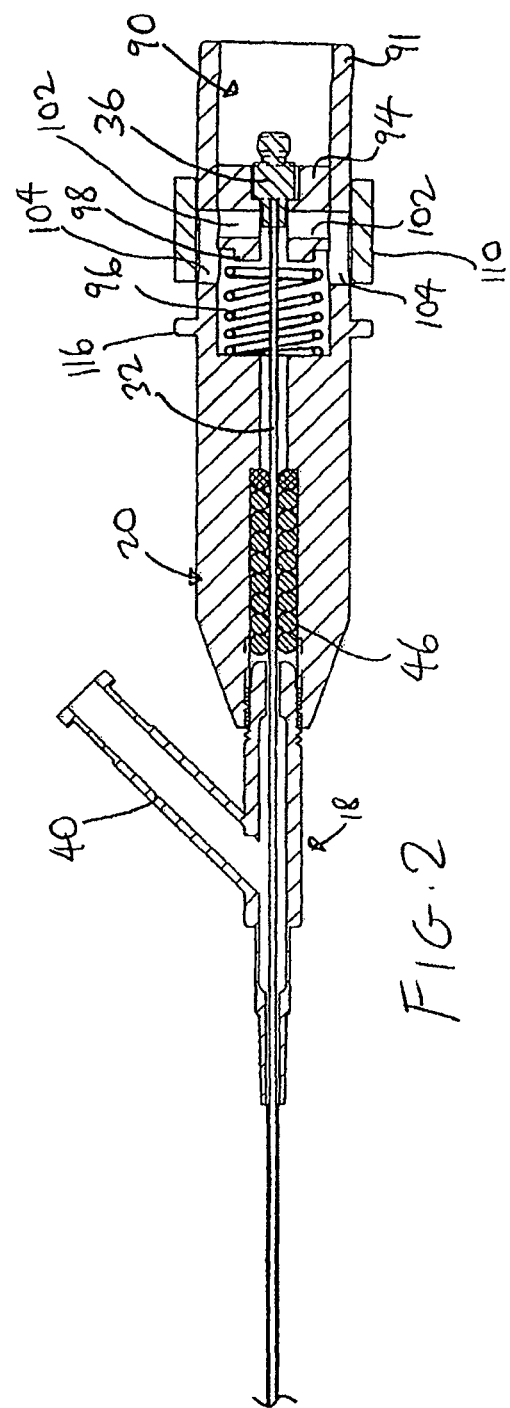

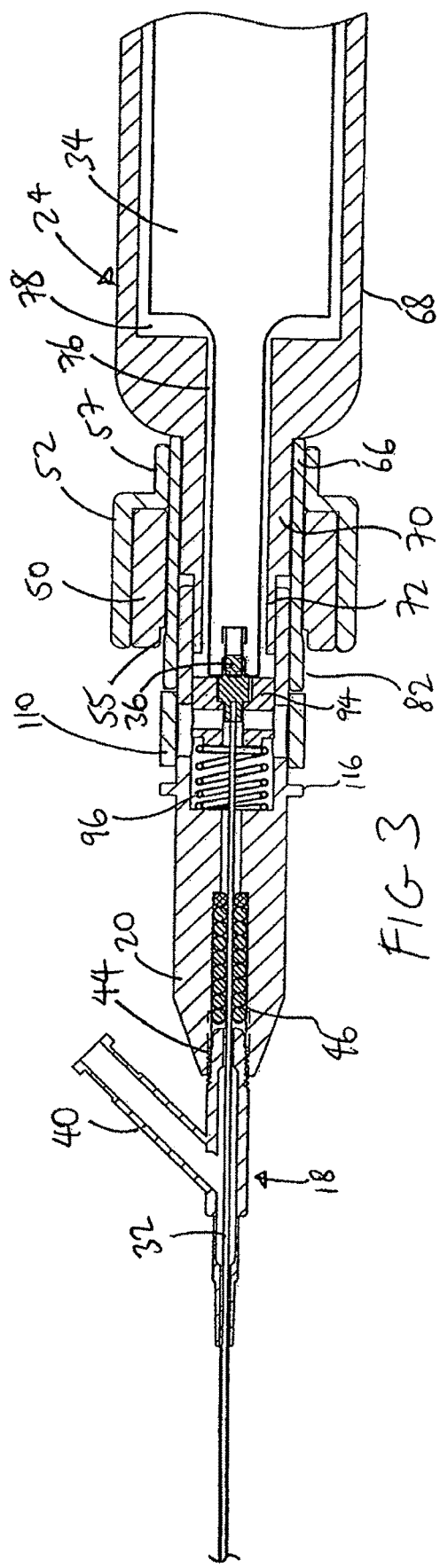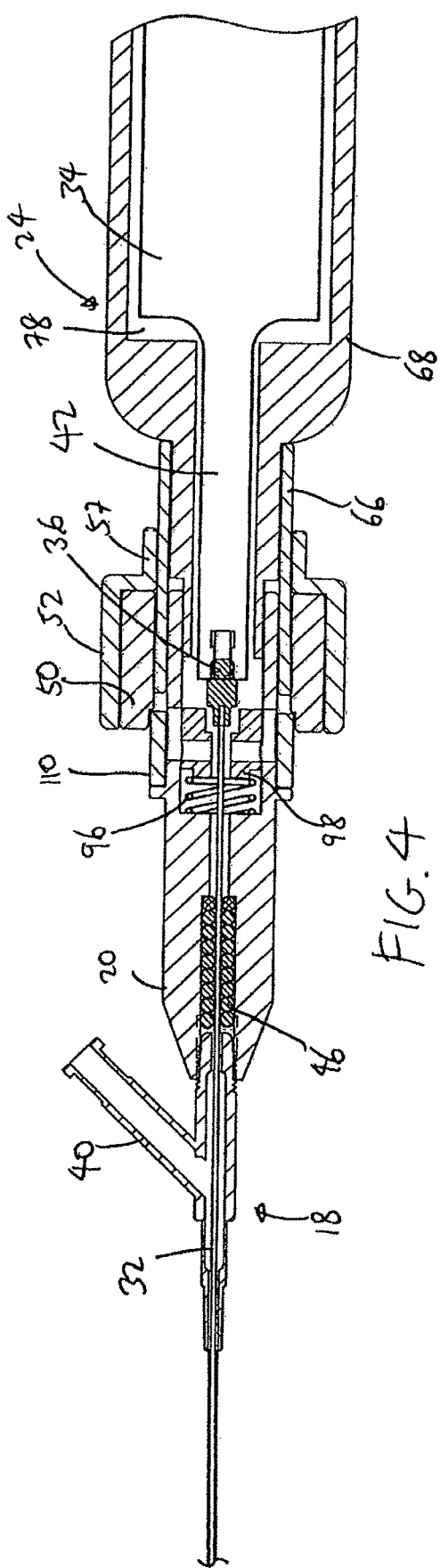

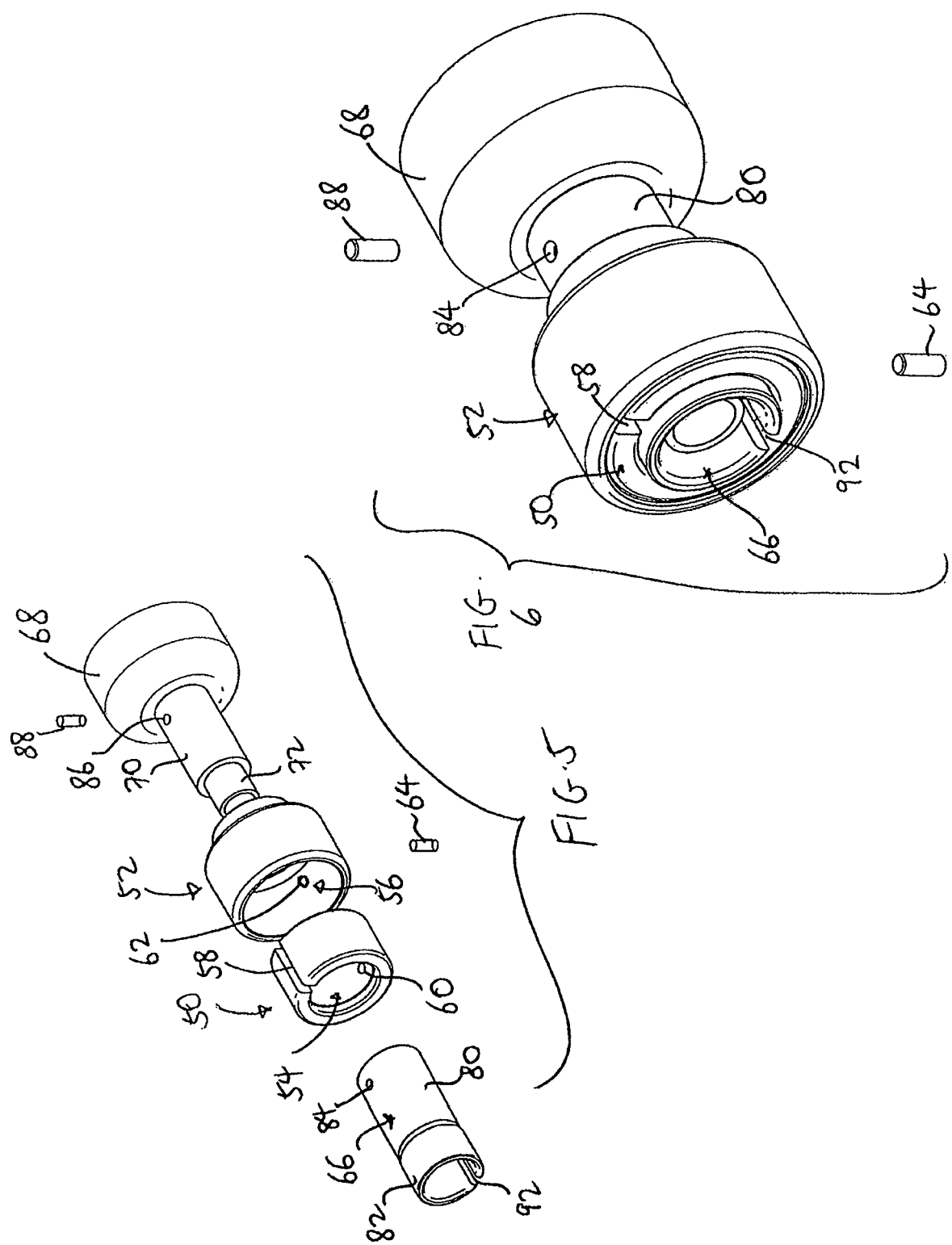

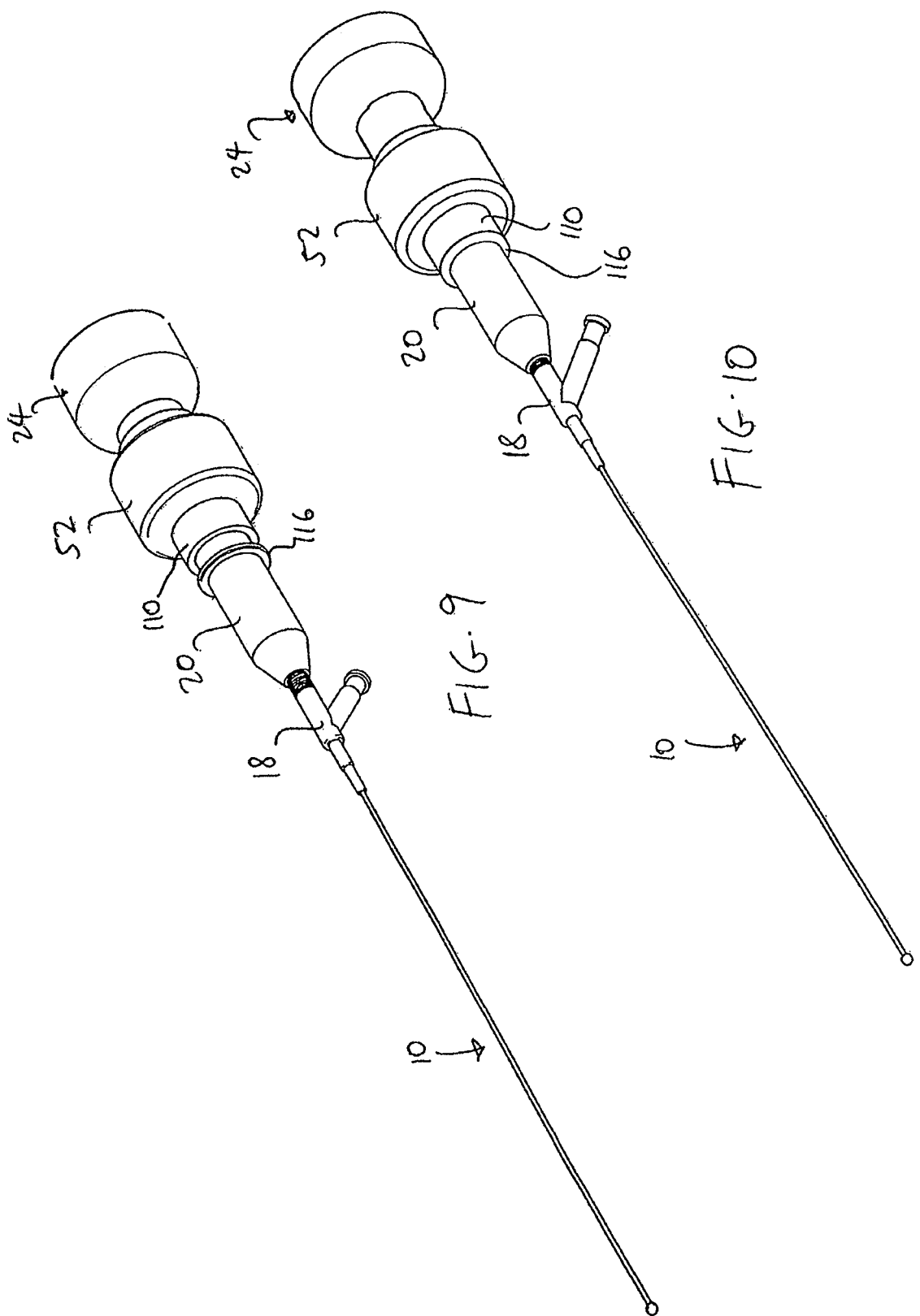

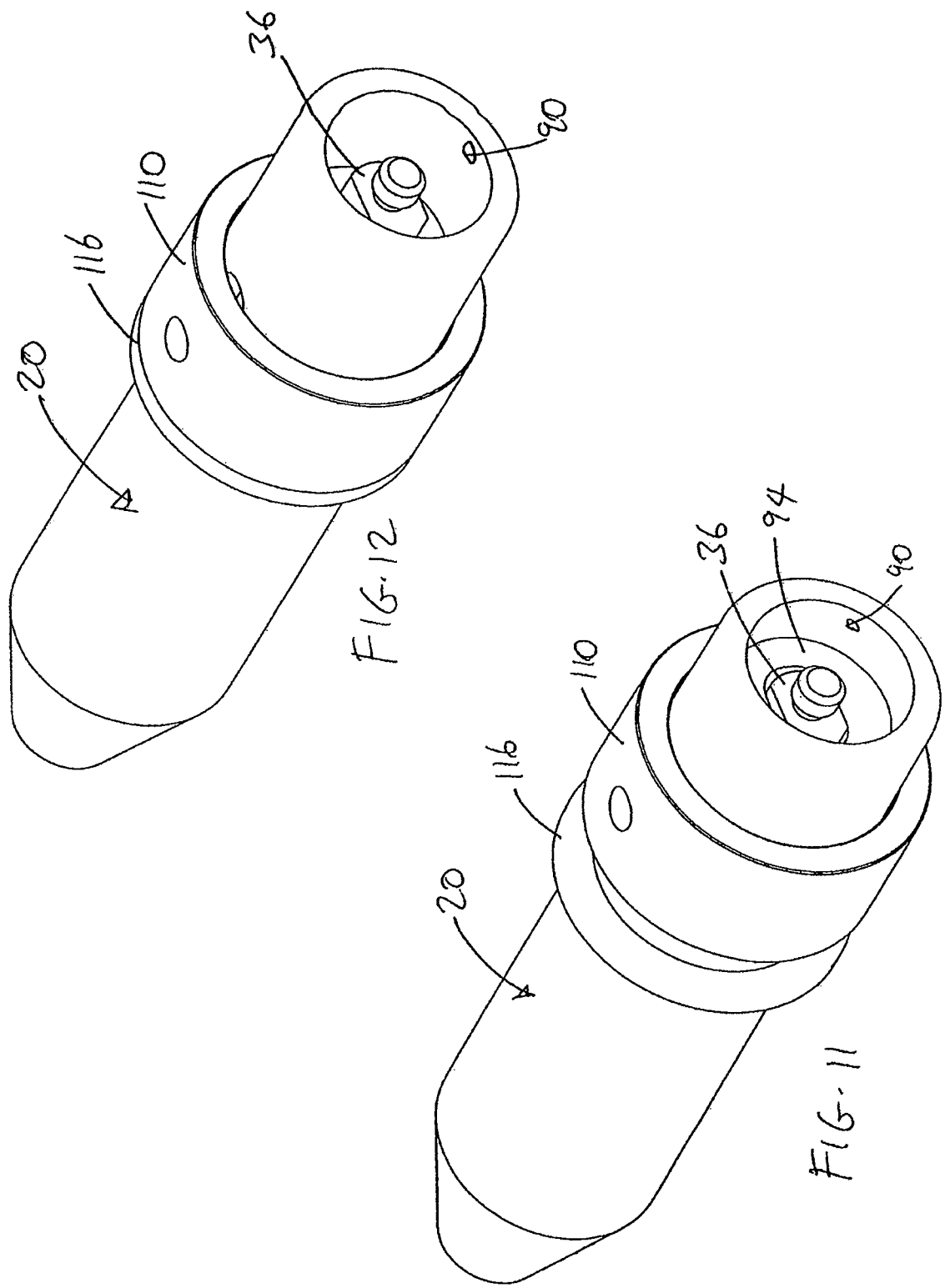

CONNECTOR FOR SECURING ULTRASOUND CATHETER TO TRANSDUCER

CROSS-REFERENCE TO RELATED APPLICATIONS

This application is a continuation of U.S. patent application Ser. No. 15/256,233, filed Sep. 2, 2016, now U.S. Pat. No. 10,349,964, which is a continuation of U.S. patent application Ser. No. 14/169,009, filed Jan. 30, 2014, now U.S. Pat. No. 9,433,433, which is a continuation of Ser. No. 12/831,883, filed Jul. 7, 2010, now U.S. Pat. No. 8,641,630, which is a continuation of Ser. No. 11/192,749, filed Jul. 29, 2005, entitled "Connector for Securing Ultrasound Catheter to Transducer" (now U.S. Pat. No. 7,758,510), which is a continuation of Ser. No. 10/666,459, filed Sep. 19, 2003, entitled "Connector for Securing Ultrasound Catheter to Transducer" (now U.S. Pat. No. 6,942,620), each of which is incorporated by reference as though set forth fully herein.

BACKGROUND OF THE INVENTION

Field of the Invention

The present invention pertains to medical equipment, and more particularly, to a device and method for attaching an ultrasound catheter to an ultrasound transducer which prevents frequency shifts and minimizes the mechanical impact of the handling connection area during a medical procedure.

Description of the Related Art

A number of ultrasound systems and devices have heretofore been proposed for use in ablating or removing obstructive material from blood vessels. Ultrasound catheters have been utilized to ablate various types of obstructions from blood vessels of humans and animals. Successful applications of ultrasound energy to smaller blood vessels, such as the coronary arteries, require the use of relatively small diameter ultrasound catheters which are sufficiently small and flexible to undergo transluminal advancement through the tortuous vasculature of the aortic arch and coronary tree. These ultrasound catheters incorporate a very small diameter ultrasound transmission member which extends through such catheters. The proximal end of the ultrasound transmission member is typically connected to an ultrasound transducer via a sonic connector.

The attachment of the ultrasound transmission member to an ultrasound transducer plays a very important role in ultrasound energy propagation. The attachment region needs to be accurately aligned and free of mechanical stress and other interfaces. For example, undesirable stress at the attachment region can be caused by pressing upon, pushing, pulling, torquing, bending or bumping the attachment region during use of the ultrasound catheter. In addition, it is preferable for the sonic connector to be free from any interface (i.e., contact) with any other component during energy transmission. Otherwise, such stresses and interfaces can negatively impact the propagation of ultrasound energy through the ultrasound transmission member. Contact of the sonic connector with any other part of the catheter housing during the delivery of ultrasound energy might also cause a shift in frequency and impact performance.

Thus, there still exists a need for an improved connection of the proximal end of the ultrasound transmission member to an ultrasound transducer.

SUMMARY OF THE INVENTION

It is an object of the present invention to provide an improved connection between the ultrasound catheter and the ultrasound transducer.

It is yet another object of the present invention to improve the propagation of ultrasound energy by limiting and minimizing the impact of undesirable external forces.

In order to accomplish the objects of the present invention, there is provided an ultrasound system and method of using the ultrasound system during a medical procedure. The ultrasound system has an ultrasound transducer having a transducer housing and a horn provided at the distal end of the transducer housing, an ultrasound transmission member, a sonic connector that is connected to the horn and the proximal end of the ultrasound transmission member, and a catheter knob having a proximal end that is coupled to the distal end of the transducer housing. The catheter knob has a proximal bore that houses the sonic connector. The system also includes a nesting piece that is retained inside the proximal bore of the catheter knob. The nesting piece can be moved from a first position where the sonic connector is received inside the nesting piece to a second position where the sonic connector is separated from the nesting piece when ultrasound energy is being propagated through the ultrasound transmission member.

BRIEF DESCRIPTION OF THE DRAWINGS

FIG. 1 is a perspective view of an ultrasound system according to one embodiment of the present invention.

FIG. 2 is a cross-sectional view of the Y-connector and catheter knob of the system of FIG. 1.

FIG. 3 is a cross-sectional view of the Y-connector, the catheter knob, the slide collar assembly and the transducer housing of the system of FIG. 1 with the slide collar assembly in the non-supporting position.

FIG. 4 is a cross-sectional view of the Y-connector, the catheter knob, the slide collar assembly and the transducer housing of the system of FIG. 1 with the slide collar assembly in the supporting position.

FIG. 5 is an exploded perspective view of some of the elements of the slide collar assembly of the system of FIG. 1.

FIG. 6 is an assembled perspective view of the elements of FIG. 5.

FIG. 9 is a perspective view of the system of FIG. 1 with the slide collar assembly in the non-supporting position.

FIG. 10 is a perspective view of the system of FIG. 1 with the slide collar assembly in the supporting position.

FIG. 11 is a perspective view of the catheter knob of the system of FIG. 1 with the slide collar assembly in the non-supporting position.

FIG. 12 is a perspective view of the catheter knob of the system of FIG. 1 with the slide collar assembly in the supporting position.

DETAILED DESCRIPTION OF THE PREFERRED EMBODIMENT

Figure 7:
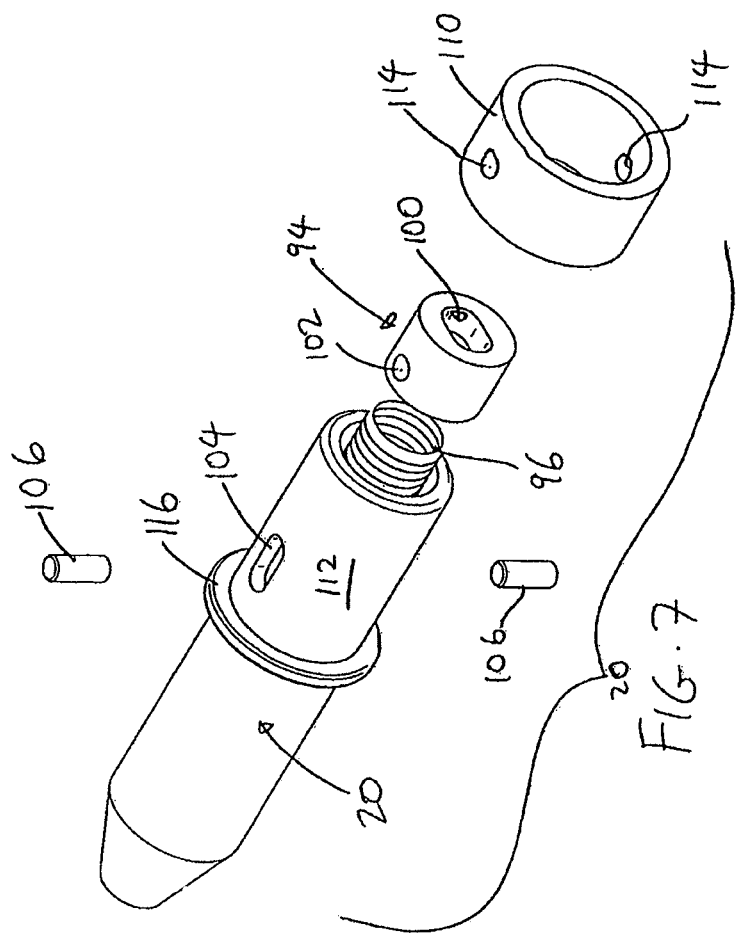
FIG. 7 is an exploded perspective view of the catheter knob of the system of FIG. 1.
Figure 8:
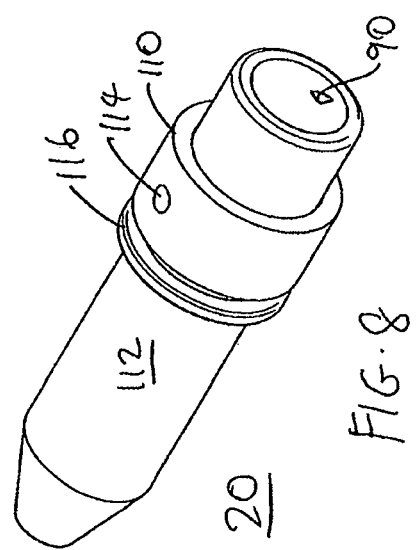
FIG. 8 is an assembled perspective view of the catheter knob of FIG. 7.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

FIG. 1 illustrates an ultrasound system according to the present invention for use in ablating and removing occlusive material inside the vessel of an animal or human being. The ultrasound system includes an ultrasonic catheter device 10 which has an elongate catheter body 12 having a proximal end 14, a distal end 16, and defining at least one lumen extending longitudinally therethrough. The ultrasound catheter device 10 is operatively coupled at its proximal end 14, by way of a Y-connector 18, a catheter knob 20, and a slide collar assembly 22, to an ultrasound transducer housing 24 As shown in FIGS. 3-4, an ultrasound transducer 34 is housed inside the transducer housing 24. The ultrasound transducer 34 is connected to a signal generator 26, which can be provided with a foot actuated on-off switch 28. The signal generator 26 can be supported by an IV pole 27. When the on-off switch 28 is depressed, the signal generator 26 sends an electrical signal to the ultrasound transducer 34, which converts the electrical signal to ultrasound energy. Such ultrasound energy subsequently passes through the catheter device 10 and is delivered to the distal end 16.

Referring also to FIGS. 2-4, an ultrasound transmission member 32 extends through the lumen of the catheter 10 from the distal end 16 to the proximal end 14. The ultrasound transducer 34 is coupled via a sonic connector 36 (described in greater detail below) to the ultrasound transmission member 32, so that the ultrasound energy can be passed through the sonic connector 36 and the ultrasound transmission member 32 to be delivered to the distal end 16 of the catheter 10. A guidewire 30, which can be any conventional monorail or over-the-wire guidewire, may be utilized in conjunction with the catheter 10 in a manner that is well-known in the catheter art.

The frontal portion of the Y-connector 18 is connected to the proximal end 12 of the catheter 10 using techniques that are well-known in the catheter art. An injection pump (not shown) or IV bag (not shown) can be connected, by way of an infusion tube (not shown), to an infusion port or sidearm 40 of the Y-connector 18. The injection pump can be used to infuse coolant fluid (e.g., 0.9% NaCl solution) into and/or through the lumen of the catheter 10. Such flow of coolant fluid may be utilized to prevent overheating of the ultrasound transmission member 32 extending longitudinally through the lumen of the catheter 10. Such flow of the coolant fluid through the lumen of the catheter 10 serves to bathe the outer surface of the ultrasound transmission member 32, thereby providing for an equilibration of temperature between the coolant fluid and the ultrasound transmission member 32. Thus, the temperature and/or flow rate of coolant fluid may be adjusted to provide adequate cooling and/or other temperature control of the ultrasound transmission member 32. In addition to the foregoing, the injection pump may be utilized to infuse a radiographic contrast medium into the catheter 10 for purposes of imaging.

Examples of iodinated radiographic contrast media which may be selectively infused into the catheter 10 via the injection pump are commercially available as Angiovist 370 from Berlex Labs, Wayne, N.J. and Hexabrix from Malinkrodt, St. Louis, Mo.

The proximal end of the ultrasound transmission member 32 is attached to the sonic connector 36 which is configured to effect operative and removable attachment of the proximal end of the ultrasound transmission member 32 to the distal horn 42 of the ultrasound transducer 34. The sonic connector 36 is preferably configured and constructed to permit passage of ultrasound energy through the ultrasound transmission member 32 with minimal lateral side-to-side movement of the ultrasound transmission member 32 while, at the same time, permitting unrestricted longitudinal forward/backward vibration or movement of the ultrasound transmission member 32.

The ultrasound transmission member 32 may be formed of any material capable of effectively transmitting the ultrasonic energy from the ultrasound transducer 34 to the distal end 16 of the catheter 10, including but not necessarily limited to metal, plastic, hard rubber, ceramic, fiber optics, crystal, polymers, and/or composites thereof. In accordance with one aspect of the invention, all or a portion of the ultrasound transmission member 32 may be formed of one or more materials which exhibit super-elasticity. Such materials should preferably exhibit super-elasticity consistently within the range of temperatures normally encountered by the ultrasound transmission member 32 during operation of the catheter 10. Specifically, all or part of the ultrasound transmission member 32 may be formed of one or more metal alloys known as "shape memory alloys". Such superelastic metal alloys are well-known in the art and will not be described in any further detail herein.

The proximal end of the Y-connector 18 is attached to the distal end of the catheter knob 20 by threadably engaging the proximal end of the Y-connector 18 inside a threaded distal bore 44 at the distal end of the catheter knob 20. O-rings 46 are provided in the threaded distal bore 44 to minimize transverse vibrations. The proximal end of the catheter knob 20 receives the extension 70 of the transducer housing 24 and is supported by the slide collar assembly 22. The slide collar assembly 22 is positioned over the distal end of the transducer housing 24, and has a non-supporting position where the slide collar assembly 22 is retracted towards the transducer housing 24; and has a supporting position where the slide collar assembly 22 is extended to cover at least a portion of the catheter knob 20. Thus, the slide collar assembly 22 functions as a support member that is disposed on the transducer housing 24 to support at least a portion of the catheter knob 20.

Referring also to FIGS. 5 and 6, the slide collar assembly 22 has an inner ring 50 (also referred to as collar 50) and an outer ring 52 (also referred to as collar 52). The inner ring 50 has a bore 54 and a longitudinal slit 58 that extends through the length of the inner ring 50. The distal portion of the bore 54 can be stepped as shown at 55 (see FIG. 3) to function as a pushing surface that pushes a nesting piece 94 (described below) in a distal direction as the inner ring 50 is moved from the non-supporting position to the supporting position. The outer ring 52 also has a bore 56, and has a narrowed proximal end 57. The inner ring 50 is retained inside the bore 56 of the outer ring 52 and abuts the narrowed proximal end 57 which acts as a stop to limit the proximal movement of the inner ring 50. Each of the inner ring 50 and the outer ring 52 has an opening 60 and 62, respectively, that are aligned with each other and that are adapted to receive a locking pin 64. A tubular inner sleeve 66 extends through the inside of the bore 54 of the inner ring 50 to ensleeve the first extension 70 of the transducer housing 24, as explained below. The sleeve 66 has a proximal section 80 and an enlarged distal section 82. The inner ring 50 is normally fitted around the proximal section 80 when the slide collar assembly 22 is in the non-supporting position, but the inner ring 50 is fitted around the distal section 82 when the slide collar assembly 22 is in the supporting position. Thus, providing the distal section 82 in an enlarged configuration allows for the inner ring 50 to achieve a friction-fit with the distal section 82, while the inner ring 50 experiences a loose fit over the proximal section 80.

The transducer housing 24 has a cylindrical wall 68 having a distal extension that comprises two stepped cylindrical extensions 70 and 72 extending from the distal end of the cylindrical wall 68. The first extension 70 is attached to the distal end of the cylindrical wall 68, and has a greater outer diameter than the second extension 72 that is attached to the distal end of the first extension 70. A throughbore 76 extends from the hollow interior 78 of the cylindrical wall 68 and through the extensions 70 and 72. The throughbore 76 can have the same diameter throughout its length. The second extension 72 is adapted to be received inside the proximal bore 90 of the catheter knob 20, while the first extension 70 is received inside the sleeve 66. In addition, an opening 84 is provided in the proximal section 80 of the sleeve 66 and is aligned with a corresponding opening 86 on the first extension 70, with the openings 84, 86 adapted to receive a locking pin 88 that secures the sleeve 66 to the first extension 70 at a fixed position.

A longitudinal slot 92 is provided on the sleeve 66. When the slide collar assembly 22 is in the non-supporting position (i.e., inner ring 50 positioned over the proximal section 80), the slot 92 is opened. However, when the slide collar assembly 22 is moved to the supporting position, the inner ring 50 is positioned over the distal section 82 and compresses the enlarged distal section 82 to close the slot 92. With the slot 92 closed, the sleeve 66 provides a frictional grip of the proximal end 91 of the catheter knob 20.

Referring now to FIGS. 2-4 and 7-8, the catheter knob 20 has a proximal bore 90 that can be sleeved over the second extension 72 in a manner such that the outer surface of the catheter knob 20 can be substantially flush with the outer surface of the first extension 70 (as best shown in FIGS. 3 and 4). The proximal bore 90 houses the sonic connector 36 and a nesting piece 94. An elastic element 96, such as a spring, is seated in the distal part of the proximal bore 90, and has one end carried on a projection 98 provided at the distal end of the nesting piece 94. The nesting piece 94 has a generally cylindrical configuration and has a receptacle 100 which functions to selectively retain the sonic connector 36, as will be explained in greater detail below. In addition, a control ring 110 is positioned around the outer surface 112 of the catheter knob 20. The control ring 112 cooperates with the nesting piece 94 to move the nesting piece 94 in a reciprocal manner inside the proximal bore 90 of the catheter knob 20, as explained below.

The nesting piece 94 has two opposite and aligned openings 102; only the top opening 102 is shown in FIG. 7, but the bottom opening is the same and is aligned on a straight line with the top opening 102. Similarly, the catheter knob 20 has two opposite and aligned channels 104; only the top channel 104 is shown in FIG. 7, but the bottom channel is the same and is aligned on a straight line with the top channel 104. In addition, the control ring 110 has two opposite and aligned openings 114. The channels 104 and the openings 102, 114 are aligned, as best shown in FIGS. 3 and 4. Two opposing pins 106 are provided, with each pin 106 adapted to be fitted inside a corresponding set of channel 104 and openings 102, 114, so as to couple the control ring 110 and the nesting piece 94 as a unitary moving piece. The width of the channels 104 define the distal and proximal limits of movement for the control ring 110 and the nesting piece 94. The catheter knob 20 also has an annular flange 116 provided about its outer surface 112 that also defines the distal limit of the movement of the control ring 110.

In use, the sonic connector 36 is shown in FIGS. 3-4 as connecting the transducer horn 42 (e.g., with a threaded connection) with the ultrasound transmission member 32. The sonic connector 36 is always located at a fixed position inside the proximal bore 90 of the catheter knob 20. When the slide collar assembly 22 is in the non-supporting position shown in FIGS. 3, 9 and 11, the elastic element 96 normally biases the nesting piece 94 in the proximal direction so that the sonic connector 36 is received inside the receptacle 100 of the nesting piece 94 to be supported by the nesting piece 94. The proximal movement of the nesting piece 94 will cause the pins 106 to move in the proximal direction inside the channels 104, thereby causing the control ring 110 to move proximally away from the flange 116. The outer ring 52 and the inner ring 50 are positioned completely over the proximal section 80 of the sleeve 66, with the narrowed proximal end 57 positioned adjacent the cylindrical wall 68 of the transducer housing 24.

When the slide collar assembly 22 is now moved from the non-supporting position to the supporting position shown in FIGS. 4, 10 and 12, the user pushes the outer ring 52 in the distal direction. The step 55 on the distal end of the inner ring 50 engages the proximal end of the control ring 110 and pushes the control ring 110 in the distal direction. Movement of the control ring 110 in the distal direction will cause the pins 106 to move in the distal direction inside the channels 104, thereby causing the nesting piece 94 to counter the bias of the elastic element 96 and move in the distal direction. As the nesting piece 94 moves in the distal direction, the sonic connector 36 becomes free from the receptacle 100 of the nesting bore 94. In addition, the distal movement of the inner ring 50 will cause the inner surface of the inner ring 50 to engage the enlarged distal section 82 of the sleeve 66, which functions to close the slot 92 so as to frictionally grip the proximal portion 91 of the knob 20 when the slide collar assembly 22 is in the supporting position. The flange 116 and the width of the channels 104 function as stops to limit the distal movement of the control ring 110.

In the supporting position, the sonic connector 36 is not supported by the nesting piece 94 so that the sonic connector 36 can be free from any component or material interfaces, thereby promoting improved ultrasound energy propagation. The medical procedure can then be carried out while the slide collar assembly 22 is in the supporting position. Upon completion of the medical procedure, the above-described steps are reversed. In particular, the combined inner and outer rings 50, 52 (slide collar assembly 22) are retracted in the proximal direction so that they are now positioned over the proximal section 80 of the sleeve 66. The bias of the elastic element 96 will push the nesting piece 94 in the proximal direction so that the sonic connector 36 is received inside the receptacle 100 of the nesting piece 94. In addition, the proximal movement of the nesting piece 94 will cause the pins 106 to move in the proximal direction inside the channels 104, thereby causing the control ring 110 to move proximally away from the flange 116. Now, the catheter 10 can be disconnected from the transducer 34.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. An ultrasonic system, comprising:
   an ultrasound transducer housing containing a transducer horn configured to be connected to a signal generator;
   an ultrasonic catheter that includes an ultrasound transmission member having a proximal end and disposed in the lumen, a sonic connector that connects the proximal end of the ultrasound transmission member with the transducer horn, a control ring, and a nesting piece configured to selectively receive the sonic connector, the control ring operatively coupled to the nesting piece to move the nesting piece; and
   a transducer mechanism configured to move from a first position to a second position, and wherein the transducer mechanism is configured such that movement of the transducer mechanism from the first position to the second position engages the control ring on the catheter to move the nesting piece.

2. The ultrasonic system of claim 1, wherein in the first position, the sonic connector is received inside the nesting piece, and in the second position, the sonic connector is separated from the nesting piece.

3. The ultrasonic system of claim 1, wherein the ultrasonic catheter includes a catheter knob having a proximal end that is coupled to a distal end of the transducer housing, the catheter knob having a proximal bore that houses the sonic connector, the nesting piece being retained inside the proximal bore of the catheter knob.

4. The ultrasonic system of claim 3, wherein the transducer mechanism includes a slide collar assembly that is positioned over a distal end of the transducer housing, the slide collar assembly being movable between a non-supporting position and a support position, wherein when the slide collar assembly is in the non-supporting position the slide collar assembly is configured to not grip the catheter knob, and when the slide collar assembly is in the support position, the slide collar assembly provides a frictional grip of the catheter knob.

5. The ultrasonic system of claim 4, wherein the slide collar assembly includes an outer collar and an inner collar, the slide collar assembly movable from a retracted position where the outer collar and inner collar are spaced apart from the control ring, to an extended position where the inner collar engages and pushes the control ring.

6. The system of claim 5, wherein the inner collar has a first bore and the outer collar has a second bore, with the inner collar received inside the second bore of the outer collar, and wherein the proximal end of the control ring is positioned inside the first bore of the inner collar when the inner collar is in the extended position.

7. The ultrasonic system of claim 6, wherein the slide collar assembly includes a sleeve partially retained inside the first bore of the inner collar, the sleeve having a longitudinal slot, and wherein each of the inner collar and the outer collar has an opening, with a pin extending through the opening in the inner collar and the opening in the outer collar.

8. The ultrasonic system of claim 7, wherein the longitudinal slot is opened when the slide collar assembly is in the non-supporting position and the slot is closed when the slide collar assembly is in the supporting position, and wherein the sleeve grips the catheter knob when the slot is closed.

9. The ultrasonic system of claim 8, wherein when the slide collar assembly is in the non-supporting position, the combined inner collar and the outer collar are retracted in a proximal direction so that the inner collar is positioned over the proximal section of the sleeve, wherein a bias of an elastic element will push the nesting piece in the proximal direction so that the sonic connector is received inside the nesting piece.

10. The ultrasonic system of claim 9, wherein the proximal movement of the nesting piece will cause the control ring to move proximally so that the ultrasonic catheter can be disconnected from the transducer housing.

11. The ultrasonic system of claim 4, wherein when slide collar assembly is in the supporting position, the sonic connector is not supported by the nesting piece so that the sonic connector can be free from any component or material interfaces, thereby promoting improved ultrasound energy propagation.

12. The ultrasonic system of claim 3, wherein the catheter knob has a longitudinal channel, and wherein each of the nesting piece and the control ring has an opening, with a pin extending through the opening in the nesting piece and the opening in the control ring, and the pin traveling within the longitudinal channel, and further comprising an elastic element to push the nesting piece in the proximal direction so that the sonic connector is received inside the nesting piece, and wherein the proximal movement of the nesting piece will cause the control ring to move proximally so that the ultrasonic catheter can be disconnected from the transducer housing.

13. The ultrasonic system of claim 1, wherein the sonic connector and the transducer horn are joined by a threaded connection.

14. The ultrasonic system of claim 1, wherein the sonic connector and the transducer horn are joined by a frictional connection.

* * * * *